United States Patent [19]

Green et al.

[11] 4,171,377

[45] Oct. 16, 1979

[54] OPHTHALMIC SOLUTION OF TRANEXAMIC ACID

[75] Inventors: Keith Green, Augusta, Ga.; Seymour F. Trager, Plainview, N.Y.

[73] Assignee: Burton, Parsons & Co., Inc., Washington, D.C.

[21] Appl. No.: 932,795

[22] Filed: Aug. 11, 1978

[51] Int. Cl.$^2$ ............... A61K 9/20; A61K 31/74; A61K 31/79

[52] U.S. Cl. ............... 424/319; 424/78; 424/80

[58] Field of Search ............... 424/319, 78, 80

[56] References Cited

U.S. PATENT DOCUMENTS

| | | | |
|---|---|---|---|
| 3,268,405 | 8/1966 | Nagasawa et al. | 424/319 |
| 3,574,721 | 4/1971 | Melander et al. | 424/319 |
| 3,639,626 | 2/1972 | Nagasawa et al. | 424/319 |
| 3,720,775 | 3/1973 | Loeffler | 424/319 |
| 3,767,789 | 10/1973 | Rankin | 424/78 |
| 3,950,405 | 4/1976 | Okano et al. | 424/319 |

OTHER PUBLICATIONS

Chem. Abst. 69, 58299(v) (1968)–Yamasaki et al.
Chem. Abst. 77 14028(s) (1972)–Nakahara.
Acta Opthalmologica (Kbh) 55, 665–673 (1977).
Acta Opthalmologica (Kbh) 56, 121–126 (1978).

*Primary Examiner*—Douglas W. Robinson
*Attorney, Agent, or Firm*—Fidelman, Wolffe & Waldron

[57] ABSTRACT

An ophthalmic solution is provided for the treatment of corneal swelling and the healing of epithelial wounds. The solution is an aqueous solution of tranexamic acid which may contain optionally, other eye-treating ingredients.

11 Claims, No Drawings

OPHTHALMIC SOLUTION OF TRANEXAMIC ACID

BACKGROUND OF THE INVENTION (a) Field of the Invention

This invention relates to an ophthalmic solution designed for and adapted to general use in the eyes of humans and domestic animals. More specifically, the patent invention relates to an ophthalmic solution which reduces swelling of the cornea.

(b) Description of the Prior Art

The only prior art use of tranexamic acid in ophthamology is the work reported in Acta Ophthalmologica (Kbh) vol. 55, pages 665–673 (1977) and Acta Ophthalmologica (Kbh) vol. 56, pages 121–126 (1978). In these papers it is reported that tranexamic acid when given orally to man is helpful in relieving the symptoms of bullous keratopathy subsequent to Fuchs endothelial dystrophy, as well as severely impeding post-surgical corneal edema often found after cataract surgery. Tranexamic acid has been used as an antifibrinolytic agent in man at dose levels up to 1 gram administered orally three times daily (total daily dose, 3 grams). It is not known whether the rate of uptake of the drug from the intestine allows the attainment of plasma levels as high as 25 µg/kg, which is the theoretical maximum from a 1 gram oral dose.

Tranexamic acid,

trans-4-(aminomethyl) cyclohexanecarboxylic acid (AMCHA) has been the subject of investigations and patents relating to its effect in suppressing the activity of plasmin in vivo. See for example, Merck's Index, 9th Edition, Merck and Co., publishers, Rahway, N.J., 1976, item 9259 on page 1230, U.S. Pat. Nos. 3,268,405, 3,574,721, 3,639,626 and 3,950,405. None of this prior art work suggested the use of tranexamic acid for reducing swelling of the cornea.

SUMMARY

This invention consists of aqueous solutions of therapeutically effective amounts tranexamic acid adapted to be applied topically to a swollen cornea and reduce the swelling and to enhance epithelial healing. The tranexamic acid preferably is in a concentration of from about 2 to 10 weight percent in an aqueous solution which may contain other eye treating components. Thus, the tranexamic acid may be dissolved in Ringer's solution, which is an isotonic solution of sodium, potassium and calcium chlorides and may have added buffer solutions necessary to regulate the pH, plus sugars.

Particularly desirable base solutions are the ophthalmic solutions described in U.S. Pat. No. 3,767,788 to Rankin, which is hereby incorporated by reference. This patent describes aqueous ophthalmic solutions containing about 0.05 to 2 percent by weight of polyethylene oxides having molecular weights of at least 100,000 to provide a viscosity of 0 to about 30,000 cps at 20° C., plus polyalkylene glycols, preferably polyethylene glycol, in amounts ranging from 500 to 5000 weight percent based on the weight of the polyethylene oxide, together with other optional components. As recited in said patent there may be included: pH buffers such as sodium borate or mono and disodium phosphates, or salts such as other alkali-metal phosphates, carbonates and acetates; mechanical buffers or viscosity controlling agents such as water soluble eye compatible cellulose derivatives; eye compatible non-ionic surfactactants; polyvinyl pyrrolidone; and eye compatible biocides.

Tranexamic acid solutions provide a greater rate of healing of corneal lesions and therefore offer an advantage over other treatment modalities currently available to enhance healing of corneal wounds. The advantage of an ophthalmic solution is that the drug is delivered to the target organ, viz the eye, rather than relying upon absorption from the intestine with the large number of variables associated with this route of administration (e.g. possible breakdown by stomach acids and enzymes, whether taken before or after a meal, variability in gastro-intestinal motility and absorption along different parts of the intestine). An ophthalmic solution offers delivery directly to the eye and especially to the ocular surface, and will allow penetration of the drug into the eye where healing enhancement may also exist. In addition, with an ophthalmic solution a lower dose is required to be administered compared to that required by the oral route. Furthermore, as the results indicate tranexamic acid not only enhances the healing process but also reduces corneal edema often associated with corneal lesions.

DESCRIPTION OF THE PREFERRED EMBODIMENT

To show the effect of tranexamic acid solutions in reducing corneal swelling and in healing epithelial wounds, the following tests were conducted in living rabbits.

EXAMPLE

Twenty-four living adult rabbits, weighing 2 to 2.5 kg each, were given topical anesthesia, 0.5% proparacaine hydrochloride, in their eyes. A demarcated lesion 6 mm in diameter was made in each corneal epithelium using a trephine and scraping off the epithelium within the demarked zone.

Eight rabbits (the controls) were treated with Adsorbotear alone in each eye (test animals A). Adsorbotear is an ophthalmic solution available from Burton Parsons Chemicals, Inc., Washington, D.C. and comprises polyethylene oxide, polyethylene glycol, a buffer, a cellulose derivative and thimerosal. Eight rabbits were treated in one eye with Adsorbotear alone and the other eye with Adsorbotear containing 2% by weight tranexamic acid (test animals B). Eight rabbits were treated as in the immediate preceeding, but with 5% by weight tranexamic acid (test animals C).

The eyes of each rabbit were treated four times daily at 2½ hour intervals with a 50 µl drop of Adsorbotear alone, or with a 50 µl drop of Adsorbotear vehicle containing 2 or 5 percent by weight of tranexamic acid, as was applicable. The 2 percent solution amounted to 1 mg of tranexamic acid/50 µl and the 5 percent was 2.5 mg/50 µl.

Although all corneas appeared to be at approximately the same thickness at twenty-four hours the average percentage reductions in thickness in the 24 to 48 hour interval of the eyes treated with tranexamic acid was as follows:

Table 1

| Test Animals Medication | A (control) Absorbotear alone | B Adsorbotear & 2% tranexamic acid | C Adsorbotear & 5% tranexamic acid |
|---|---|---|---|
| Reduction in Thickness, Percent | 23 | 33 | 29 |

The average percentage reduction in the eye paired to the treated eye as in Table 1 was as follows:

Table 2

| Test Animals | A (control) | B | C |
|---|---|---|---|
| Reduction in Thickness, Percent | 23 | 31 | 29 |

The above data show (Table 1) that both the 2% and 5% tranexamic acid solution accelerate the rate at which corneal thickness returns to normal and that the paired Adsorbotear-only treated eye also showed a greater return to normal thickness (Table 2). It is apparent from these data that there is also a systemic effect of tranexamic acid, since its application in one eye results in an improvement in both eyes.

The average rate of healing of the lesions also increased due to the presence of tranexamic acid. During the time interval between 6 and 36 hours the following lesion healing rates were observed in the control animals and in the tranexamic acid treated eyes of the test animals in group B and C.

| Test Animals Medication | A (control) Adsorbotear alone | B Adsorbotear & 2% tranexamic acid | C Adsorbotear & 5% tranexamic acid |
|---|---|---|---|
| Healing, Percent | 75.5 | 76.5 | 82.5 |

The average healing rates with the Adsorbotear-only treated eyes in B and C are given in table 4.

Table 4

| Test Animals | A | B | C |
|---|---|---|---|
| Healing, Percent | 75.5 | 76 | 88.5 |

Systemic effects are present in lesion healing since the paired non-drug treated eyes in test animals B and C also showed improvement over the control animals. Similar improvements were obtained with tests animals using a 10% tranexamic acid solution.

The use of Adsorbotear and the other ophthalmic solutions of U.S. Pat. No. 3,767,788 as the vehicle provides a therapeutic effect in addition to the antiswelling activity of the tranexamic acid. A synthetic mucous layer is provided which serves as an artificial tear material and the solution may contain biocides and other medicinal agents as set forth in U.S. Pat. No. 3,767,788.

Without wishing to be bound by any theory, the mechanism of action appears to be a stimulation of the endothelial fluid pump mechanism of the cornea.

What is claimed:

1. A method for treating an eye having corneal epithelial wounds comprising topically applying to the cornea an aqueous ophthalmic solution comprising a therapeutically effective amount of tranexamic acid, whereby swelling in the cornea is reduced and the healing of epithelial wounds is enhanced.

2. The method of claim 1 wherein the amount of tranexamic acid in the aqueous ophthalmic solution is from about 2 to about 10 percent.

3. The method of claim 2 wherein the aqueous ophthalmic solution comprises an isotonic solution of sodium, potassium and calcium chlorides.

4. The method of claim 3 wherein the percent by weight of tranexamic acid is about 2%.

5. The method of claim 3 wherein the percent by weight of tranexamic acid is about 5%.

6. The method of claim 3 wherein the percent by weight of tranexamic acid is about 10%.

7. The method of claim 2 wherein the aqueous ophthalmic solution is an aqueous solution comprising about 0.05 to about 2.0% by weight of an ethylene oxide polymer having a molecular weight of at least 100,000 and in an amount sufficient to provide a vicosity of 0 to about 30,000 cps at 20° C., and from about 100 to about 5000 weight percent based on the ethylene oxides polymer of a polyalkylene glycol, said solution containing in addition from 0 to an effective amount of an eye compatible pH buffer, from 0 to about 0.5% of an eye-compatible nonionic surfactant, from 0 to 5% by weight of polyvinyl pyrrolidone and from 0 to an effective amount of an eye compatible biocide.

8. The method of claim 7 wherein the polyalkylene glycol is polyethylene glycol.

9. The method of claim 8 wherein the percent by weight of tranexamic acid is about 2%.

10. The methd of claim 8 wherein the percent by weight of tranexamic acid is about 5%.

11. The method of claim 8 wherein the percent by weight of tranexamic acid is about 10%.

* * * * *